United States Patent [19]

Rees et al.

[11] Patent Number: 5,498,525
[45] Date of Patent: Mar. 12, 1996

[54] METHODS FOR RAPID MICROBIAL DETECTION

[75] Inventors: Catherine E. D. Rees; Katalin Rostas-Mulligan, both of Nottingham; Simon F. Park, Macclesfield; Stephen P. Denyer, Lewes; Gordon S. A. B. Stewart, Leicester; Sabah A. A. Jassim, Nottingham, all of Great Britain

[73] Assignee: Amersham International plc, United Kingdom

[21] Appl. No.: 839,766

[22] PCT Filed: Aug. 8, 1991

[86] PCT No.: PCT/GB91/01354

§ 371 Date: Apr. 9, 1992

§ 102(e) Date: Apr. 9, 1992

[87] PCT Pub. No.: WO92/02633

PCT Pub. Date: Feb. 20, 1992

[30] Foreign Application Priority Data

Aug. 9, 1990 [GB] United Kingdom ............... 9017443

[51] Int. Cl.[6] .................... C12Q 1/02; C12Q 1/66; C12Q 1/68; C12Q 1/70
[52] U.S. Cl. .................... 435/29; 435/5; 435/6; 435/8; 435/252.3; 435/69.1; 435/69.7; 435/69.8
[58] Field of Search ............... 435/5, 6, 252.3, 435/69.1, 69.7, 8, 69.8, 29

[56] References Cited

FOREIGN PATENT DOCUMENTS

| | | |
|---|---|---|
| 0168933 | 1/1986 | European Pat. Off. . |
| WO89/03878 | 5/1989 | WIPO . |
| WO90/04037 | 4/1990 | WIPO . |
| WO90/04041 | 4/1990 | WIPO . |

OTHER PUBLICATIONS

Hirotanmi et al. "Inactivation of T5 phage . . . " FEMS Microbiol. 77:pp. 13–18 1991.

Glover "Principles of Gene Cloning" *Gene Cloning* pp. 1–20 1984.

Boylan et al. "Fused Bacterial Luciferase . . . " JBC. 1989 vol. 264, No. 4 pp. 1915–1918.

Science, vol. 218, No. 4567, Oct. 1, 1982, pp. 791–793.

Technique—A Journal of Methods in Cell and Molecular Biology, vol. 2, No. 4, Aug. 1990, pp. 194–201.

*Primary Examiner*—Robert A. Wax
*Assistant Examiner*—Hyosuk Kim
*Attorney, Agent, or Firm*—Wenderoth, Lind & Ponack

[57] ABSTRACT

A method of testing for target bacteria involves adding bacteriophage to a sample to infect the bacteria in the sample; killing extracellular bacteriophage without at the same time killing phage-infected bacteria; amplifying bacteriophage remaining in the sample; and causing the bacteriophage to infect reporter bacteria and thereby produce an observable signal. The reporter bacteria are genetically engineered to have an indicator gene which on expression gives rise to a detectable signal, wherein expression of the indicator gene is initiated on bacteriophage infection of the bacteria.

7 Claims, 2 Drawing Sheets

FIG. 1

THE PLASMID pSB292, CONTAINING THE pCK1 GRAM POSITIVE REPLICON AND A PROMOTERLESS COPY OF THE luxAB GENES. TL ENCODES THE Lambda $TL_1$ TRANSCRIPTION TERMINATOR

FIG.2

METHODS FOR RAPID MICROBIAL DETECTION

FIELD OF THE INVENTION

This invention concerns methods for the detection of microbial organisms, e.g. bacteria and bacteriophage in a wide variety of cases such as foods, clinical specimens and environmentally important samples. The invention can also be applied to examine susceptibility to antibacterial compounds and the effectiveness of virucidal agents.

BACKGROUND OF THE INVENTION

The detection and identification of bacteria is of great interest in a variety of microbiological applications. For example the need to screen food, water and other beverages for pathogenic bacteria is crucial in ensuring consumer safety. The determination of levels of certain families of bacteria is a commonly used approach to estimating the shelf life and microbial acceptability of such products and hygienic status of the processing equipment and raw materials used in their manufacture. The diagnosis of microbial infections also relies on the detection of the causative organism. The screening of environmental waters for organisms such as Legionella has recently assumed considerable importance.

The desire to detect bacteriophages (viruses which specifically infect bacteria) stems from their ability to kill bacteria and hence the deleterious effect they can have on the fermentation of milk, for example, by killing the starter culture bacteria. Bacteriophages are also used, e.g. in the water industry, as tracers to determine the rate of river flow or sewage leakage.

The methods available to carry out bacterial detection and enumeration suffer from a number of drawbacks. Traditional culture based methods form the backbone of the tests used but as they rely on bacterial growth, often in selective media that allows the desired organism to grow while suppressing the growth of other bacteria, they are inherently slow; a total viable count taking 18–24 hours and detection of Salmonella taking 4–7 days. In many cases bacterial numbers may be under-estimated because their particular growth requirements may not be met by the media provided or they may have been sub-lethally injured or entered a stress induced physiological state in which they are viable but not culturable. Culture based methods are not suitable for on-site testing due to the long incubations required.

A variety of methods have been proposed to address these drawbacks and allow rapid bacterial detection, some claimed to be applicable to on-site use. For example, the measurement of adenosine triphosphate (ATP), an intracellular component of all living things, provides a rapid methodology but this is not specific and hence offers, at best, an estimation of the total bacterial population.

Immunoassay approaches with antibodies specific for the desired bacteria have failed to achieve widespread use because of inadequate specificity and sensitivity leading to the need for two days of enrichment culture before the immunoassay in the case of a Salmonella test, for example. Interference from competing organisms and the sample matrix have led to unacceptable rates of false positive and false negative results and protocols that are not substantially shorter than culture.

Methods based on DNA or RNA probes have been applied to bacterial detection but currently suffer from the problem of involving complicated protocols, unpleasant chemicals in some of the solutions and the need for elevated temperature. They certainly are not user friendly to technicians trained in classical microbiology. Together with immunoassays and nucleic acid amplification strategies such as the Polymerase Chain Reaction (PCR) they do not distinguish between live and dead bacteria. This makes them unsuitable for direct assays (where there is no culture step to allow the amplification of the living organisms) of the viable bacteria. In certain applications this distinction is very important e.g. when disinfectants have been used to ensure that there are very few living Legionella in a water system, it is meaningless to use an assay which fails to discriminate and detects the organisms which have been killed by the disinfection process.

There are a number of approaches that rely on expensive instruments to speed up the detection of bacteria. An example of these is impedance/conductance measurement where the bacterial presence is detected by their metabolism of complex nutrients to simpler chemicals with a concomitant change in the electrical properties of the medium. Such methods are highly capital intensive and inappropriate for small laboratories or on-site use.

Microscopy techniques, possibly employing selective staining, are limited in sensitivity and generally offer poor differentiation between living and dead bacteria. Routine microscopy will only permit presumptive identification based on morphology unless combined with selective culture or immunological staining.

In view of the above, it is highly desirable to have methods for the detection of bacteria and bacteriophages that are simple to perform, specific, rapid (providing results in hours rather than days), able to detect only living organisms, capable of on-site use and without the need for an expensive instrument. Preferably the assays would be performed on a wide variety of sample types without pre-treatment and with a minimum number of steps. The assay result should be a detectable event that is easily observed and amenable to automated reading. It would be further desirable if the assays were able to detect disabled bacteria which might otherwise require a pre-enrichment culture step and a selective enrichment step for detection. Non-culturable but viable organisms should also be detected.

DESCRIPTION OF PRIOR ART

Many of the methods to identify microbial organisms have been based on classical microbiology using nutrient agar plates. In recent years attempts to use molecular biology and genetic modification have also been applied to this area. In particular Ulitzur and Kuhn (European patent application 0168933) introduce a detectable marker, often the enzyme luciferase, into bacteriophages which can then be used for bacterial detection. Modified phages are added to samples suspected of containing the bacteria of concern which is a host for that bacteriophage. If a suitable bacterial host is present then bacteriophage nucleic acid will infect that host and will be expressed in the bacteria. When the modified bacteriophage carries the marker luciferase then the presence of the bacteria can be determined by the emission of light which can be easily measured.

PCT/90/04041 by DNA Plant Corporation uses a different marker system i.e. ice nucleation and also a panel of phages to allow typing.

PCT90/04037 uses genetically modified microorganisms as indicators in a test system for the detection of a range of toxic substances.

PCT89/03878 describes a system based on genetic modification which can be applied to eukaryotic viruses.

U.S. Pat. No. 4,797,363 uses bacteriophages which have been labelled with a variety of signal systems. However, the labelling is by direct chemical methods and does not depend on expression of additional genes.

ADVANTAGES OF THE NEW INVENTION

In systems based on genetic modification using bacteriophage to detect bacteria, the genetic modification has been to the bacteriophage. For various technical reasons this is not always an easy modification to make. If a panel of phages is required for bacterial identification then each phage of the panel will need the similar modification and so the problem is multiplied. One embodiment of this invention allows use of non-genetically modified bacteriophages with the later use of a modified (or panel of modified) bacteria carrying the detectable marker. It is technically far easier to modify the bacteria compared with the bacteriophage.

SUMMARY OF THE INVENTION

The invention comprises several methods for the testing and the detection of bacteria or bacteriophages in a sample. It also allows the susceptibility of bacteria to antibacterial agents to be determined and the effectiveness of virucidal agents to be assessed. Both qualitative and quantitative testing are encompassed.

This is achieved by exploiting the interaction between bacteriophages and bacteria. The way in which a bacteriophage infects a bacterium can be used to develop assays. The interaction is specific and once this recognition/binding event has taken place, the bacteriophage injects its nucleic acid into the host bacterium. The host is then used to replicate the 'phage' being produced and, upon breaking open the host, to then infect additional bacteria.

Once the phage has specifically infected the cell and injected its nucleic acid, it is protected from the extracellular environment. Part of the invention makes use of this to kill or remove those phages which have not specifically infected a bacterium. Therefore if the sample contains, say, Salmonella then the specific phage will be protected, if Salmonella is absent no phage will be protected. The removal or killing of unbound phage can be achieved by a variety of methods for example virucidal agents, heat, removal of chemicals essential for phage stability etc.

This aspect is clearly very different from other diagnostic approaches using phages where a directly or indirectly labelled phage is allowed to bind to the surface of a bacterium and unbound is washed away prior to developing a signal (enzymatic, fluorescent, luminescent, etc.). In this case all the important events occur outside the cell contrasting clearly with the present invention.

The next stage of the invention depends on the number of cells being detected. The number of bacteriophages protected and able to replicate and emerge may be sufficient to be detected directly. If not the number can be amplified by growing them on a propagating host for the required time (this can be short since phage generation times are less than 1 hour and 10–1000 progeny are produced).

Once the number of phages is adequate for detection, this can be achieved by a number of methods e.g. immunologically with an antibody to some component of the phage or with a nucleic acid probe to the phage genome or by plaque assay. A preferred method is based on the discovery that a bacterium can be constructed by genetic modification that has the potential to produce a detectable signal (gene(s) coding for a phenotype that can be readily detected) but this potential is only expressed when the bacterium is infected by a phage. The phage triggers the signal generation and hence the presence of the phage (and therefore of the bacterium that protected it) can be detected sensitively and easily. These bacteria, herein called reporter bacteria, are new materials per se and constitute another aspect of the invention.

DETAILED DESCRIPTION

The invention thus includes several methods of testing which involve the use of one or both of two key features. One key feature is the killing of extracellular bacteriophage in a fluid sample which also contains phage-infected bacteria. The other key feature is the provision of reporter bacteria which are genetically engineered to have an indicator gene which on expression gives rise to a detectable polypeptide, Expression of the indicator gene is initiated only on bacteriophage infection of the bacteria. The nature of the indicator gene, and the means used to detect the detectable polypeptide, are not material to the invention.

There follows sections describing these two key features. These are then followed by a description of various methods of testing according to the invention.
Differential phage killing Hirotani et al. (1991) described the anti-viral activity of unsaturated fatty acids and related alcohols against T5 phage. With the addition of 3000 lux (Lumens per square meter) illumination, they achieved 97.6% inactivation of T5 phage with C18:2 linoelaidic acid (LA) at 50 µg/ml. We have demonstrated that a protocol along these lines achieves the differential phage killing that we desire. The fluid sample containing this acid or alcohol addition is subjected to photon irradiation, fluorescent light being perfectly suitable. If monochromatic light is used, the wavelength is preferably around 420 nm, although a subsidiary effect is seen at around 530 nm. Illumination of sufficient time and intensity is effective to selectively kill extracellular bacteriophage, without adversely affecting phage which have infected bacteria in the sample.

An alternative treatment for differential phage killing involves addition to the sample of a C1 to C4 carboxylic acid such as acetic acid. The acetic acid concentration in the sample is preferably from 0.01 to 1.0%, particularly 0.1 to 0.5%, the figures being expressed as percent by volume of glacial acetic acid in the sample. If the concentration is too low, extracellular bacteriophage are not killed; if the concentration is too high, infected bacteria in the sample may be damaged. The sample is incubated for a time to permit the acetic acid to effect virucidal action, e.g.37° C. for 15 minutes, and is then brought back to approximate neutrality by the addition of base. Vinegar (5%) has been used in place of acetic acid with very Similar results.

After killing extracellular bacteriophage, it is often necessary to amplify surviving phage (present within infected bacteria) in the sample. However, it appears that bacteriophage infection of bacteria at ambient or higher temperatures may sensitise the bacteria to subsequent exposure to acetic acid, so that the bacteria subsequently fail to amplify the phage properly. A preferred solution to this problem is to effect bacteriophage infection of bacteria in the sample at a temperature below ambient. For example, the sample can be held at 0° C. in an ice-bath. Phage infection takes place efficiently even at these low temperatures, and the resulting infected bacteria are no longer sensitive to the acetic acid treatment.

For those organisms which are themselves acid sensitive, e.g. pseudomadaceae, such treatment may not be effective. A possible alternative treatment involves use of a mixture of hydrogen peroxide and sodium hydroxide.

Preparation of Reporter Bacteria

Successful bacteriophage (phage) infection generally requires the sequential expression of sets of genes. Studies of a number of bacteriophages have identified a variety of biological strategies for obtaining temporal regulation (e.g. see Rabussay and Geiduschek, 1977; McKnight and Tjian, 1986). Most of these strategies involve transcriptional control. The classically described strategies operate at initiation of transcription (Jacob and Monod, 1961; Ptashne, 1986).

In an alternative mechanism, first described for phage Lambda, the same promoters used for transcription of genes expressed early in the infection are used to transcribe genes expressed later through a process of antitermination of transcripts (Roberts, 1969). Operons exhibiting this type of control are arranged so that genes located promoter-proximal to the termination signal can be expressed maximally while genes promoter-distal to the termination signal are unexpressed or poorly expressed. These latter sets of genes are expressed when some physiological or developmental change eliminates the activity of the termination signal. The nature of the termination signals and the nature of the antitermination factors vary greatly (Platt, 1986).

Using the tools and techniques of molecular microbiology, it is possible to dissect a bacteriophage genome and to clone elements of that genome into autonomously replicating plasmid vectors. Among a library of such randomly generated constructs, those containing a bacteriophage promoter could express promoter proximal genes; always providing that the promoter utilised the normal rifampicin sensitive bacterial RNA polymerase. If the cloned bacteriophage DNA contained a termination signal in addition to a promoter, genes proximal to the promoter would be expressed but genes distal to the promoter terminator would not. These promoter distal genes could only be expressed if the correct bacteriophage encoded antitermination signal were provided and this may well be absent on the cloned segment of DNA. The transacting antitermination factor could be provided, however, as a natural part of the temporally controlled gene expression commensurate with bacteriophage infection. In other words plasmid-cloned, promoter-distal genes that are downstream of a transcription terminator could be expressed only during bacteriophage infection. If the naturally occurring bacteriophage genes are replaced by an indicator gene, such as luxAluxB, whose product is easily monitored, then phage dependent antitermination will result in expression of the indicator gene phenotype. For a construct employing luxAluxB this would mean that the initial plasmid vector construct would be dark but that during bacteriophage infection bioluminescence would result. Although luxAluxB expression and bioluminescence is a preferred indicator system, other indicator systems that facilitate monitoring a trans-acting antitermination event following bacteriophage infection could be employed.

Existing knowledge of the molecular architecture and gene control mechanisms of bacteriophages such as Lambda Ø80, P2, P22, Hk022 and 21 would allow those skilled in the art to identify specific DNA regions to be isolated in vitro for engineering a construct as defined above. This 'in depth' knowledge, although helpful, is not necessary, however, as random cloning of the genome of a genetically uncharacterised bacteriophage can provide equally effective constructs.

Figure 1:
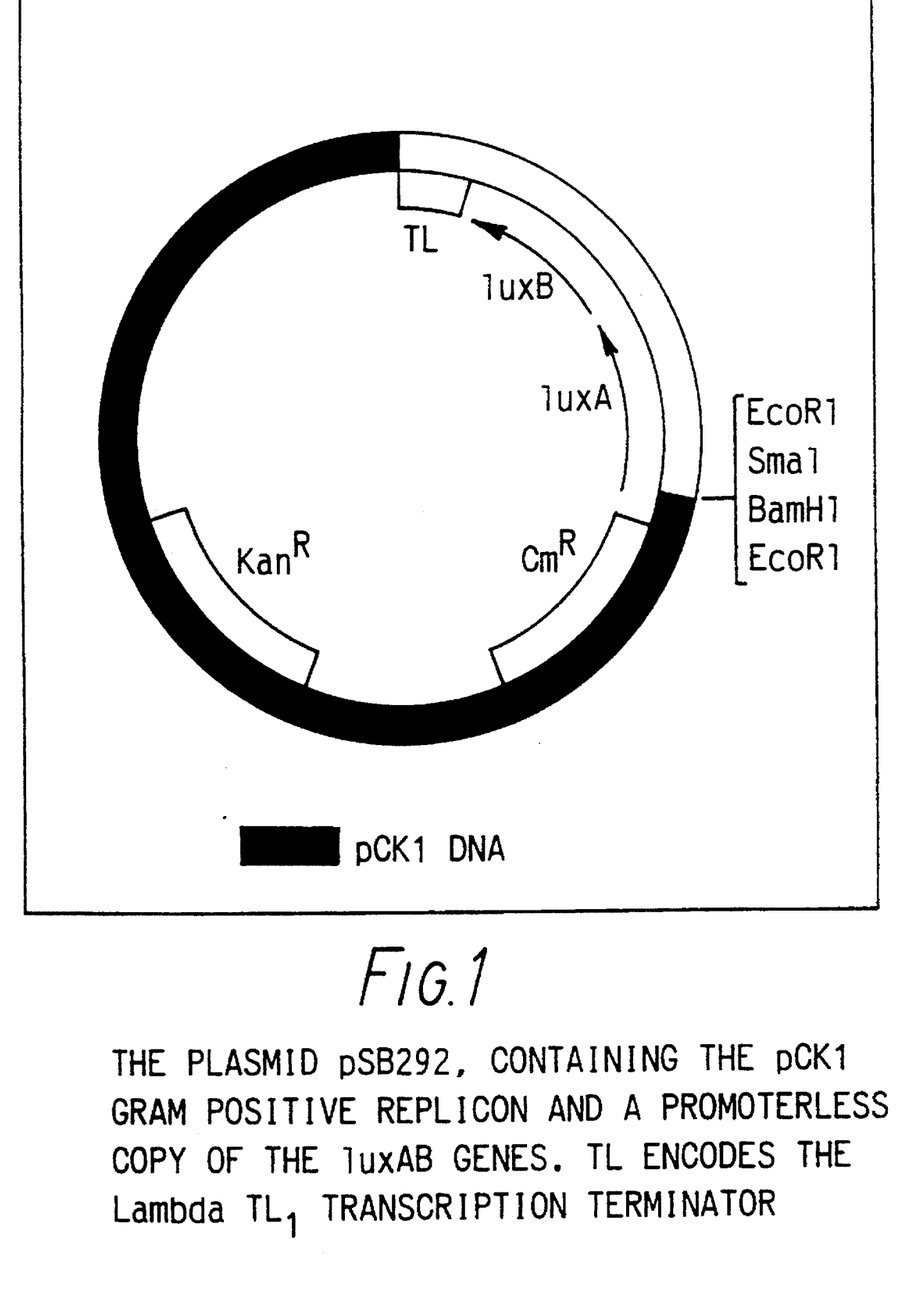
FIG. 1 depicts a map of plasmid pSB292 containing the pCK1 gram positive replicon and a promotorless copy of the luxAB genes.
Figure 2:
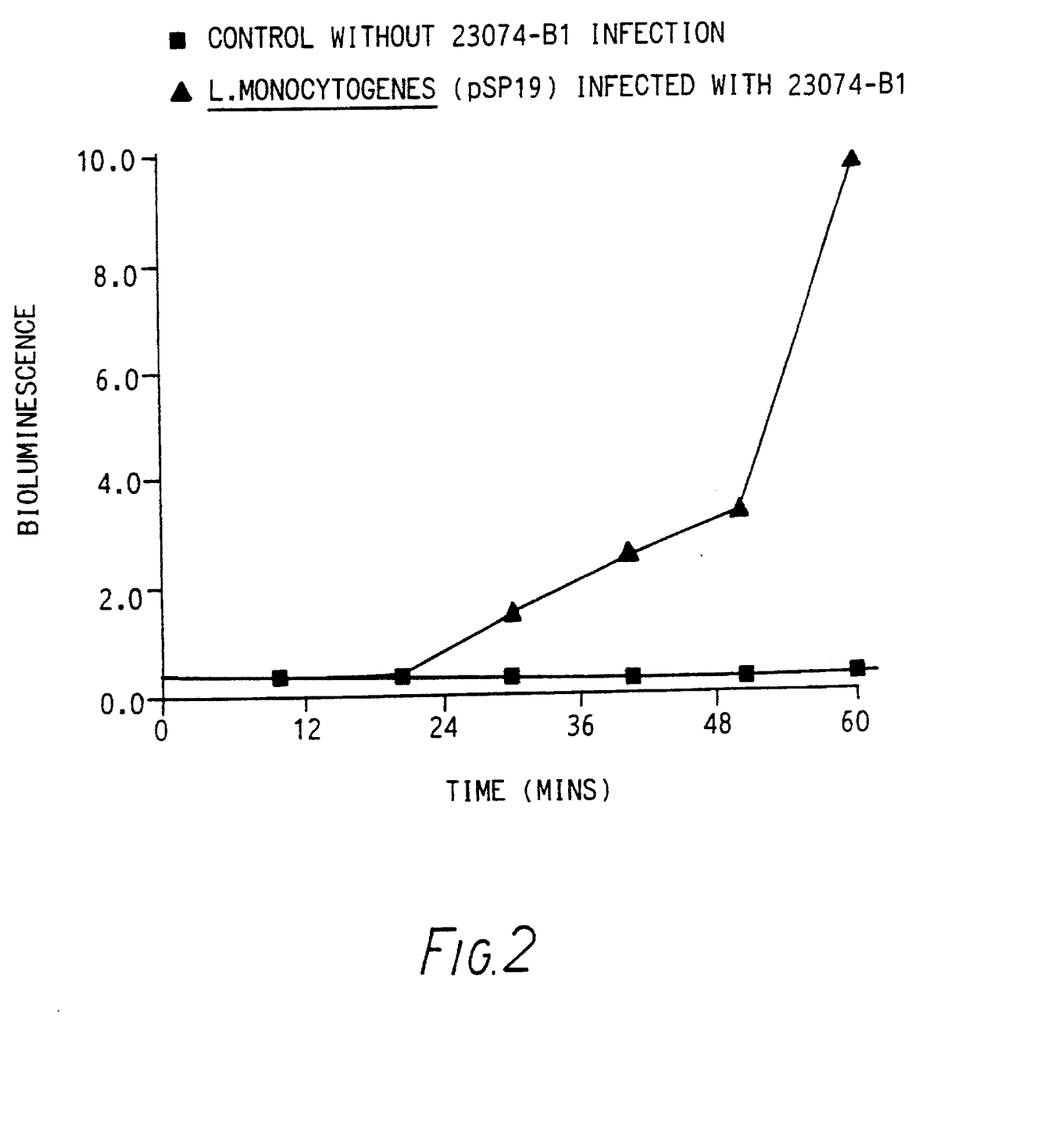
FIG. 2 depicts the bioluminescence profile of pSP19 following phage infection vs. control without infection.

The bacteriophage 23074-B1 (ATCC) is a *Listeria monocytogenes* serotype 4 phage for which the genome has not been characterised. A partial digest using the restriction enzyme Sau3a was performed on the genome of 23074-B1 and the DNA fragments ligated into the BamH1 site of plasmid pSB292, containing the pCK1 Gram positive replicon (Gasson & Anderson, 1985) and a promoterless copy of the luxAluxB genes (FIG. 1). The ligation reaction was used to transform *Listeria monocytogenes* 23074 to chloramphenicol resistance and recombinant clones were screened for a bioluminescent phenotype. Those clones having no constitutive bioluminescence (dark clones) were further screened for bioluminescence following infection with bacteriophage 23074-B1. Clones providing phage dependent bioluminescence were identified. FIG. 2 shows the bioluminescence profile of one such construct (pSP19) following phage infection. A 1000-fold difference in bioluminescence was observed between phage infected and non-infected cells. pSP19 and constructs with similar phenotypes provide the basis for detecting the presence of bacteriophage 23074B1. pSP19 was constructed with out prior knowledge of the phage genome and demonstrates the generic nature of the selection process. Other bacteriophages for *Listeria monocytogenes* could be detected using a similar protocol.

It is known that not all bacteriophages control temporal gene expression by antitermination. T7, for example, provides a new rifampicin resistant RNA polymerase that promotes transcription from novel T7 RNA polymerase-specific bacteriophage promoters (Chamberlin et al., 1970). Other phages of the T7 type would, if screened by a cloning programme as described above, nevertheless provide recombinant constructs silent for expression of the indicator gene unless infected by the corresponding bacteriophage. Such constructs would have the bacteriophage-specific RNA polymerase promoter sequence proximal to the indicator gene. The host RNA polymerase would not transcribe such a construct and hence, if the indicator used was luxAluxB, the recombinant would be dark. Bacteriophage infection would, however, lead to the temporal expression of the bacteriophage RNA polymerase and hence active transcription of the indicator gene. The use of T7, T3, T5 and SP6 phage specific RNA polymerases to control gene expression on recombinant plasmid vectors is well known (Old and Primrose, 1989). It has not, however, previously been used to enumerate bacteriophage and this element is but one possible control circuit in a generic approach to harnessing temporal expression to induce, in trans, the expression of an indicator gene.

Bacteriophage P1 is a well characterised phage that appears to use neither termination nor a specific RNA polymerase to temporally regulate phage gene expression (Yarmolinsky and Sternberg, 1988). Nevertheless, promoters have been identified from P1 that are inactive in uninduced P1 lysogens but become active about 30 min after prophage induction (ibid). It is possible to predict that these promoters would be identified in a screening procedure such as that described above for bacteriophage 23074B1. The cloning vector would have to be functional in a P1 host bacterium, but the principle of selection would be the same.

From those bacteriophage currently well characterised at the genetic level, there are none that are seen to lack elements of temporal control. It is reasonable, therefore, to postulate that such elements exist in all bacteriophages. Although mechanisms of temporal control differ, all currently identified mechanisms are amenable to the construction of bacteriophage/indicator chimeras that place indicator genes such as luxAluxB under the expression control of a temporally regulated bacteriophage gene switch. When present as a stable genetic construct in a non-phage infected host, the indicator gene will not be expressed. During phage infection, however, the bacteriophage can supply a transacting factor that activates the expression of the chimeric indicator construct. Measurement of indicator expression, for example in vivo bioluminescence if luxAluxB is employed, is a direct and quantitative measure of the presence of virulent bacteriophage particles. Although a detailed understanding of the molecular biology of a bacteriophage would assist in the construction of the chimeric indicator, the demonstration of such a construct for the L. monocytogenesphage 23074B1 shows that a chimeric indicator can be generated from an entirely uncharacterised bacteriophage. In principle, therefore, chimeric indicator constructs could be generated for any bacterium/bacteriophage couple.

These techniques give rise to reporter bacteria, namely genetically engineered bacteria constructed to have a gene switch/indicator gene chimera where activation of the switch is dependent upon a trans-acting factor supplied during phage infection. These genetically engineered bacteria may be rendered non-viable and non-culturable but retain their capacity to detect phage infection.

Various methods of testing involving use of these reporter bacteria are described in the following section.

1. The rapid detection of bacteria a) Phage amplification and assay

Bacteria such as Salmonella spp. or Listeria spp. require recovery and enrichment before detection. Enrichment to bring bacterial numbers up to a detectable level requires a time that is dependent on the rate of microbial growth and division. Increases in bacterial numbers follow an exponential curve and hence for 1 Salmonella or Listeria to reach $10^8$ bacteria respectively would take 27 divisions and, with a growth rate of 30 minutes, this would require a minimum 14 hours. By comparison, a bacteriophage infection cycle typically takes 40 minutes and produces between 10 to 100 progeny phage. A single Salmonella or Listeria infected with a lytic phage could, in the presence of additional helper bacteria, produce $10^8$ bacteriophage particles in 5.3 hours at a burst size of 10 or in 2.6 hours at a burst rate of 100. In other words, bacteriophage are amplified between 3 and 5 times as fast as bacteria. This amplification of bacteriophage could be used to detect the presence of low numbers of pathogenic bacteria in foods and other samples as follows:

25 g of food containing 1–10 pathogenic bacteria would be homogenised in growth medium and a pathogen-associated bacteriophage added at a concentration sufficient to ensure rapid infection of the pathogen (m.o.i.* of 10 or greater) (m.o.i.*: multiplicity of infection). After 10 to 15 mins to allow injection of phage DNA into the pathogen, a chemical or physical treatment would be used to destroy, remove, neutralise or inactivate all remaining bacteriophage. Examples of chemical treatment could include virucidal but sub-antimicrobial levels of biocides. Examples of physical treatment include virucidal but sub-antimicrobial levels of heat. After destruction of bacteriophage, chemical virucides would be neutralised and, if heat was utilised, temperatures returned to those optimum for microbial growth. The initial pathogens would now be phage infected and there would be no viable extracellular phage present. After a further 30 to 40 minutes of incubation the phage infection cycle in the initial pathogens would be complete and virulent bacteriophage would be released as the pathogens lyse. The numbers of bacteriophage released would be too small to detect, but these few phage could be amplified if a permissive host (not necessarily pathogenic) was added to the culture. The addition of $10^6$–$10^7$ permissive bacteria would allow amplification of 10–100 phage particles or greater in 3 to 5 hours. The presence of bacteriophage at such levels could be rapidly and conveniently detected by the bacteriophage assay format described above.

If food or other samples contain low levels of target pathogens, these pathogens will be indirectly detected by a positive bacteriophage assay following infection and amplification. The preferred assay for bacteriophage would be by via induction of a bioluminescent phenotype in a bacterium genetically engineered to contain a promoter/luxAB or luxAluxB chimera, dependent for expression on phage infection. Immunological assays for the presence of phage in the final amplified culture medium could also be considered however.

Samples that contain no target bacteria cannot protect (eclipse) any bacteriophage from the virucidal treatment. No phage would be available therefore to be amplified by the permissive bacterial host. Such samples would contain no bacteriophage in the final amplified culture and samples from such a culture would be negative in the bacteriophage assay described above.

Samples could be scored as positive or negative for a target pathogen within 3 to 6 hours on the basis of presence or absence of pathogen associated bacteriophages.

Since bacteriophages may infect and replicate in viable but non-culturable bacteria, the rapid detection of bacteria should include bacteria sublethally injured. Avoidance of any need to recover growth potential in sub-lethally injured bacteria, contributes significantly to the speed of the assay.

Bacteriophages used to detect low levels of bacteria may be either chemically treated with agents such as NaOH or be selected for natural mutations that increase their sensitivity to chemical or physical inactivation agents. Such mutants would facilitate the inactivation of residual bacteriophage after primary infection of the target bacteria and prior to amplification of those phage released from those target bacteria.

The permissive bacteria used to amplify bacteriophage released from the target bacteria, may be selected for natural mutations that attenuate any pathogenic potential and/or ability to compete effectively in the natural environment.

b) Single cycle infection and assay

Indicator microorganisms such as the enteric group of bacteria are typically present in foods and environmental samples at levels well in excess of specific pathogens. Increasing levels of indicator bacteria may be utilised as a measure of an increasing probability of the presence of pathogens and, in consequence, careful monitoring can prove of considerable value in establishing hygiene status and in HACCP monitoring (see Microorganisms in Foods 4; ICMSF). Monitoring the presence of indicator bacteria at levels of $10^2$/g or $cm^2$ would best be achieved by the phage amplification assay described above. Levels $\geq 10^3$/g or $cm^2$, however, could be assayed using a single cycle of phage infection without amplification and, in consequence, in a time scale of less than 100 min.

Samples containing indicator bacteria $\geq 10^3$/g or $cm^2$ would be treated with an indicator associated bacteriophage(s) at a concentration sufficient to ensure rapid infection of the indicator (m.o.i. of 10 or greater). After 10 to 15 min to allow infection of phage DNA into the indicator bacteria, a chemical or physical treatment would be used to destroy all remaining bacteriophage. After neutralisation of the virucidal treatment, incubation would be continued in microbial growth medium for 40–50 min to allow completion of the phage infection cycle. Bacteriophage would be released at levels of $10^4$ or greater (assuming a minimum burst size of 10). At these levels the presence of bacteriophage could be assayed for directly by the novel assay format described above without further amplification through a permissive host.

c) Competitive binding and assay

An alternative format to that described in single cycle infection and assay, could employ competitive binding of bacteriophage between the indicator bacteria present in the sample under assay and the bacteria engineered to detect the presence of phage. Given an equal concentration of natural indicator bacteria and engineered assay bacteria and subsaturating level of bacteriophage, the phage would be equally distributed between binding and infection of indicator and assay bacteria. Under these circumstances the amount of bioluminescence obtained from a luxAB assay would be half that obtained if there were no indicator bacteria present. In this format the assay time would be less than 60 min, there would be no requirement for a virucidal treatment step and, by manipulating the assay bacteria and bacteriophage ratio, a quantitative estimate of bacterial numbers could be established.

2. Rapid detection of environmental bacteriophage

The bacteriophage assay format could be designed so that the reporter bacteria were engineered to be responsive to infection by previously specified environmental bacteriophage. Such phage might include coliphage. Such an assay would allow the rapid detection of viable coliphage in water and sewage effluent. Since the assay can in principle be designed to detect any bacterium/bacteriophage couple, the detection, in situ, of any relevant bacteriophage can be contemplated.

3. Rapid evaluation of virucidal agents

The assay format of bacteriophage detection, detects only viable and infective phage, it reflects biological activity, not merely the presence of phage particles. The determination and assessment of antiviral activity in potential virucides generally require elaborate cell culture or electron microscopy facilities. Bacteriophage, as prokaryotic viruses, may be used as model virus agents to test the potency of virucidal compounds. Virucidal activity against wild type bacteriophages would be measurable as a decrease in bioluminescence following assay with a bacterium genetically engineered to contain a promoter/luxAB chimera dependent for expression on phage infection. Such a bacterium has been described herein as a novel assay format for bacteriophage.

Previously, a virucide assay using recombinant bacteriophage engineered to contain luxAB within the bacteriophage genome has been described (Jassim et al., 1990). The present invention, however, allows the use of wild type bacteriophage while retaining the expression of bioluminescence as a measure of virus viability.

The present invention is further illustrated by the following Examples:

Example 1 describes the preparation and use of reporter bacteria based on Listeria monocytogenes 23074.

Examples 2 to 5 describe techniques for killing extracellular bacteriophage, without affecting the ability of phage-infected E. coli to be subsequently amplified.

Example 6 describes the detection of Listeria by activation of reporter bacteria from Example 1 with amplified bacteriophage.

EXAMPLE 1

Promoter Cloning from the B1 Phage of Listeria Monocytogenes 23074

Isolation of Plasmid DNA and Phage DNA

Plasmid DNA was isolated by standard procedures and purified by centrifugation to equilibrium in CsCl gradients. B1 phage particles were propagated in Listeria monocytogenes ATCC 23074 and purified by banding in CsCl gradients according to Audurier et al., (1977). DNA was liberated from the phage by a phenol/chloroform extraction procedure and recovered by precipitation with ethanol in the presence of 0.3M sodium acetate.

Preparation of a B1 phage library in pSB292 for promoter screening

DNA from the B1 phage was digested separately with the restriction enzymes AluI, HaeIII, and RsaI. After the reactions had gone to completion the enzyme was removed by phenol/chloroform extraction and the DNA recovered by ethanol precipitation. In parallel, the plasmid pSB292 (FIG. 1 and Park et al. 1991) was digested with SmaI and the DNA recovered as above. A mixture of B1 phage DNA fragments was prepared by mixing equal volumes of the AluI, HaeIII and RsaI digests. These fragments were then ligated (insert/vector ratio 2:1) into the SmaI site of pSB292 using a standard ligation reaction containing 1 mM hexaminecobalt III chloride. The ligation mix was dialysed against distilled water for 30 minutes using VSWP filters (Millipore) and used to transform L. monocytogenes ATCC 23074 by the method of Park and Stewart (1990). Transformants were recovered by plating onto brain heart infusion agar (BHI, Oxoid) containing 5 µg/ml chloramphenicol and incubating overnight at 30° C.

Screening transformants for phage inducible promoters

Approximately $3\times10^3$ transformants were obtained from the B1 phage library. Transformants containing derivatives of pSB292 in which phage promoters constitutively expressed luxAB were visualised, after the addition of 20 µl dodecanol to the petri dish lid, as bioluminescent colonies using an Argus 100 VIM3 photon imaging camera (Hamamatsu Photonics). A number of "dark" transformants (350), in which the lux genes were not being expressed, were picked onto duplicate sets of BHI/chloramphenicol plates and incubated at 30° C. for 4 hrs. B1 phage (10µl containing $3\times10^8$ PFU) was then spotted onto one set of the duplicate plates and incubation continued for a further hour. The phage infected and uninfected plates were then visualised under the photon imaging camera. One transformant, which was bioluminescent only in the presence of a B1 bacteriophage infection, was considered to contain a pSB292 derivative in which a phage inducible promoter was directing expression of the lux genes. This plasmid was designated pSP19.

Promoter induction experiments

Cells containing pSP19 were grown in BHI broth containing 5 µg/ml chloramphenicol at 30° C. with shaking. When the Absorbance at 600 nm was 0.1, cells were harvested (8000 g and 30° C. for 10 min) The supernatant was discarded and the cell pellet resuspended in 1/100 of the original volume of broth. Two 0.5 ml aliquots of this suspension were removed to plastic test tubes. To one tube B1 bacteriophage was added at a multiplicity of infection of 3. Both tubes were then incubated at 30° C. for 10 min with no agitation to allow phage absorption. After this period the contents of the test tubes were transferred to separate flasks containing 50 ml of pre-warmed BHI. The cultures were then incubated under the original conditions (30° C., 150 rpm). At timed intervals, 1 ml samples were removed for cell density and cellular bioluminescence measurements. Bioluminescence was assessed by adding 0.01 vol of a 1% dodecanal solution in ethanol to samples and immediately assessing the light production in a luminometer (Turner Designs, 20).

*Listeria monocytogenes* 23074 containing the plasmid pSP19 was infected with bacteriophage 23074B1 at time zero. Increasing bioluminescence was observed with time after phage infection. The results are shown in FIG. 2.

EXAMPLE 2

Method

Phage Lambda was exposed to linoelaidic acid (LA) (50 µg/ml) in Tris-Cu buffer (1.21 g tris; 5.8 g NaCl; 0.075 g $CaCl_2$; 10 ml of 1% w/v $CuSO_4$ per liter; pH 7.4) under differing illumination conditions. These included dark, fluorescence lighting and exposure to relatively specific wavelengths by using a range of filters with transmission optima at 300, 338, 360, 375, 395, 400, 420, 450, 455 and 530 nm (Waters Associates, Inc. Manual No. 1M82902, 1980 and FIG. 3). The incident light for filter transmission was obtained from a microscope condenser. Time of exposure, temperature of exposure and the importance of $Cu^{2+}$ were assessed.

Results

At a concentration of 50 µg/ml, LA inactivated 93% of Lambda phage in 30 minutes at 37° C. (Table 1). This inactivation was not observed if samples were incubated in the dark. Significantly, either with or without illumination, *E. coli* W3110 was not affected by the unsaturated fatty acid.

ii) Glacial acetic acid solution to give final concentrations of acetic acid of 0.005, 0.05, 0.1, 0.25 and 0.5% v/v in Lambda buffer. The tubes were further incubated at 37° C. under static conditions for 15 or 30 minutes. Then the acid was neutralised by the use of 3M sodium hydroxide. Phage growth (pfu/ml) was detected by plaque formation on plates with 100 µl of sensitive host cell (10 cfu/ml).

Results are set out in Table 2 below, and indicate that rapid (15 minutes) phage killing occurs at pHs between 2.91 and 2.35, similar to results obtained for vinegar (results not shown). Again, as for vinegar, the acetic acid system was equally effective against *Listeria monocytogenes* phage.

A comparative study between 5% v/v vinegar and 0.25% v/v acetic acid showed almost equivalent phage inactivation profiles. The preferred time for bacterial exposure to phage was shown to be in the range of 5 to 50 minutes on ice, with an optimum of about 10 minutes on ice. With this protocol, bacteria are detectable in 5 hours by plaque formation, as shown in the following Table 3. Even with infection periods as long as 20 minutes on ice, there was shown to be no subsequent loss of bacterial viability during the 15 minutes treatment with vinegar or acetic acid.

The ability to use acetic acid mediated phage killing to detect *E. coli* W3110 in a mixed population of bacteria was investigated. Mixed cultures containing $10^9$ cfu/ml of *Staph.epidermis, S.arizonae, Strep.mutans, Ps.aeruginosa,* and *B.subtilis* were inoculated with differing amounts of *E. coli* W3110. Phage Lambda was employed, using the acetic acid mediated phage inactivation protocol described above, to detect specifically the *E. coli* W3110 present in the mixed cultures. Table 4 documents the results which prove that the method can be translated into practice.

TABLE 2

Effect of different concentrations and ph-values of acetic acid on the survival of phage and host cells at 37° C./15 minutes.

| % of glacial acetic acid in Lambda buffer | pH-values | cfu/ml of *E. coli* W3110 | pfu/ml of phage Lambda |
| --- | --- | --- | --- |
| 0 (Lambda buffer) | 7.4 | $3 \times 10^8$ | $3 \times 10^9$ |
| 0.005 | 4.1 | $6 \times 10^8$ | $9 \times 10^8$ |

TABLE 1

Effect of the combination of 50 µg/ml linoelaidic acid (LA) and light on the kinetic killing of phage Lambda and host cells at 37° C. for 30 minutes.

| | In the absence of light | | In the presence of fluorescent light | |
| --- | --- | --- | --- | --- |
| Microorganisms | Tris-Cu buffer deprived LA | Tris-Cu buffer supplemented LA | Tris-Cu buffer deprived LA | Tris-Cu buffer supplemented LA |
| Phage Lambda | $3 \times 10^{10}$ pfu/ml | $4 \times 10^{10}$ pfu/ml | $3 \times 10^{10}$ pfu/ml | $4 \times 10^{10}$ pfu/ml |
| *E. coli* W3110 | $3 \times 10^8$ cfu/ml | $3 \times 10^8$ cfu/ml | $4 \times 10^8$ cfu/ml | $3 \times 10^8$ cfu/ml |

EXAMPLE 3

This example illustrates the use of acetic acid as a selective virucidal agent.

Into sterile Eppendorf tubes were dispensed 8.4 µl phage of $10^9$ pfu/ml+8.4 µl of a particular dilution of host bacterial cells. This mixture was incubated on ice for 10 minutes. Then to each tube was added either:

i) Vinegar solution to give a final concentration of vinegar of 5, 10, 15 or 20% v/v in Lambda buffer, or TABLE 2-continued Effect of different concentrations and ph-values of acetic acid on the survival of phage and host cells at 37° C./15 minutes.

| % of glacial acetic acid in Lambda buffer | pH-values | cfu/ml of *E. coli* W3110 | pfu/ml of phage Lambda |
| --- | --- | --- | --- |
| 0.05 | 3.24 | $3 \times 10^8$ | $1.5 \times 10^7$ |
| 0.1 | 2.91 | $5 \times 10^8$ | $7 \times 10^3$ |

TABLE 2-continued

Effect of different concentrations and ph-values of acetic acid on the survival of phage and host cells at 37° C./15 minutes.

| % of glacial acetic acid in Lambda buffer | pH-values | cfu/ml of E. coli W3110 | pfu/ml of phage Lambda |
|---|---|---|---|
| 0.25 | 2.57 | 4 × 10$^8$ (5.7 × 10$^8$) | 0 (0) |
| 0.5 | 2.35 | 6 × 10$^7$ | 0 |

Data within brackets cfu/ml for *Listeria monocytogenes* ATCC 23074 and pfu/ml of phage 23074 B1.

TABLE 3

Number of pfu of phage 23074 B1 obtained after the infection of various number of *Listeria monocytogenes* ATCC 23074.

| Phage inactivation by: | Absence of host cell | 100 host cells | 1000 host cells |
|---|---|---|---|
| Lambda buffer | Complete lysis | Complete lysis | Complete lysis |
| 0.25% acetic acid | No plaques | 120 | 800 |
| 0.3% acetic acid | No plaques | 150 | 750 |
| 15% vinegar | No plaques | 110 | 900 |

TABLE 4

The detection of *E. coli* W3110 in complex cultures by plaque formation

| Phage inactivation regimen | Approximate cfu of E. coli W3110 in mixed culture | | |
|---|---|---|---|
| | 100 | 1,000 | 10,000 |
| 0.25% acetic acid | 111 | 700 | Complete lysis |
| 5% vinegar | 132 | 1,000 | Complete lysis |

EXAMPLE 4

Protocol

An overnight culture of *E.coli* W3110 was diluted ten-fold stepwise in Lambda buffer. 8.4 μl aliquots containing different numbers of cells were transferred in duplicate to sterile Eppendorf tubes. To this, 8.4 μl of a suspension of phage Lambda (1×10$^9$ pfu/ml) was added and the phage allowed to adsorb to the cells for 10 minutes at 0° C. Non-adsorbed phage were then inactivated by the addition of 83.2 μl of acetic acid in Lambda buffer (to give a final concentration of 0.25%) and incubation at 39° C. for 20 minutes. The acid was then neutralised by the addition of 14 μl of 0.3M NaOH (to give final pH of ≈8.0).

Unaffected phage (i.e. those protected by adsorption to W3110 cells) were then immediately titred in one of the duplicate sets by mixing with 100 μl of W3110 cells (1×10$^6$ cfu) and 3 ml of 0.6% top layer agar and poured over Luria agar plates and incubated at 37° C. Plaques were counted after 18 hrs incubation. Phage amplification for the other duplicate set, was initiated by the addition of 3 ml of FT broth and cultures incubated at 37° C. with shaking (150 rpm) for 5 hrs. Phage titres were determined by plating 100 μl samples as previously described.

Results are set out in the following Table 5.

Lambda buffer is 6 mM Tris-HCl, pH 7.8 10 mM MgSO$_4$. 7H$_2$O, 10 mM CaCl$_2$, 0.005% gelatin.

FT broth is per liter 5 g NaCl, 10 g Tryptone, 10 ml 1M MgCl$_2$, 20 ml 10% maltose.

TABLE 5

Phage Lambda infection of various numbers of *E. coli* W3110 and the amplification obtained in 5 hrs at 37° C. subsequent to external phage killing

| | Approximate cfu of E. coli W3110 | | | | |
|---|---|---|---|---|---|
| | 0 | 7 | 70 | 700 | 7000 |
| On solid medium Time zero | nil | 2 | 7 | 200 | 1000 |
| In liquid medium 5 hrs (phage amplification) | nil | 4 × 10$^5$ | 5 × 10$^5$ | 2 × 10$^6$ | 2 × 10$^9$ |

These Examples 3 and 4 describe a complete protocol whereby bacteriophage can be killed within 15 minutes, at an efficiency greater than 9 log cycles, without any detectable reduction in the number of coexistent bacterial cells or in their ability to amplify after virucidal treatment. The Examples further show that the method is applicable to a variety of bacteriophage and is effective for both Gram positive and Gram negative genera. The direct detection of bacteria by bacteriophage amplification in axenic and complex cultures is demonstrated.

Some minor variations of protocol may be necessary depending on the organism under test but the principle remains the same, as the following Example shows.

EXAMPLE 5

The technique of Examples 3 and 4 was repeated, but using *Staphyloccus aureus* NCIMB 8588 and phage NCIMB 9563. Differential phage killing was achieved using two different concentrations of acetic acid. After phage binding at 0° C., the samples were warmed to 37° C. for 5 minutes, and then cooled to 0° C. prior to acetic acid treatment. Results are set out in Table 6.

TABLE 6

| % acetic acid used for phage inactivation | Number of S. aureus cells | | | | |
|---|---|---|---|---|---|
| | 0 | 8 | 80 | 800 | 8000 |
| | Number of plaques obtained | | | | |
| 0.15% | 0 | 8 | 80 | 800 | 8000 |
| 0.25% | 0 | 8 | 80 | 800 | 8000 |

EXAMPLE 6

Detection of Listeria by Activation of Lm23074 (pSP19) with amplified Phage

Protocol

An overnight culture of *L. monocytogenes* 23074 (ATCC) containing 6×10$^8$ cells per ml was diluted ten-fold stepwise in Lambda buffer. Ten microliter aliquots containing different number of cells were transferred to sterile Eppendorf tubes and cooled on ice-water for 5 minutes. To this, 10 μl of a suspension of phage Lm23074B1 (ATCC) containing 1×10$^9$ pfu/ml was added and the phage allowed to adsorb to the cells for 10 minutes at 0° C. Non-adsorbed phage were then inactivated by the addition of 80 μl of 0.31% acetic acid in Lambda buffer and incubation at 39° C. for 20 minutes. The acid was then neutralised by the addition of 14 μl of 0.3M NaOH (to give a final pH of ≈8.0). To allow amplification of phage, 1×10$^8$ cells of the propagating strain Lm23074 in 1.4 ml of Luria broth were added to the Eppendorf and the samples incubated at 30° C. for 4 hours. The number of phage present in this culture was titred initially, directly after addition of the propagating bacteria, by spotting 10 µl samples on to a lawn of Lm23074 (this method of assay only allows titres to be determined down to $10^3$ pfu/ml). The presence of phage in the supernatant after 4 hours amplification was detected by the addition of 100 µl aliquots to 200 µl of an exponentially growing culture of Lm23074 (pSP19) at an $A_{450}$ of between 0.25 and 0.3. Infection was allowed to proceed for 60 minutes before light induction was measured.

Results are set out in the following Table 7, in which the light units recorded for each cell are given in column 3.

TABLE 7

| Initial No. of bacteria | Initial Phage titre | Light units after 4 hrs amplification |
|---|---|---|
| $6 \times 10^6$ | $1.8 \times 10^6$ | 20818 |
| $6 \times 10^5$ | $9.0 \times 10^5$ | 14243 |
| $6 \times 10^4$ | $1.8 \times 10^4$ | 4458 |
| $6 \times 10^3$ | $9.0 \times 10^2$ | 3601 |
| $6 \times 10^2$ | nd | 192 |
| 60 | nd | 1054 |
| 6 | nd | 268 |
| 0 | nd | 42 |
| 0 | nd | 32 | nd: not detectable in titre system used.

The above example shows that as few as 6 cells of *Listeria monocytogenes* can be detected in a total assay time of 5.5 hrs. This is a major advance in current rapid methods of detection.

REFERENCES

Audurier, A., Rocourt, J. and Courtieu, L. 1977 Isolement et caracterisation de bacteriophages de *Listeria monocytogenes*. Ann. Microbiol. (Inst. Pasteur), 127A, 185–198.

Chamberlin, M., McGrath, J., and Waskell, L., 1970, New RNA polymerase from *Escherichi coli* infected with bacteriophage T7, *Nature* 228: 227.

Gasson, M. J., and Anderson, P. H., 1985, High copy number plasmid vectors for use in lactic streptococci, *FEMS Microbiol. Lett.* 30: 193.

Hirotani, H., Ohigashi, H., Kobayashi, M., Koshimizu, K. & Takahashi, E. 1991 Inactivation of T5 phage by cis-vaccenic acid, an antivirus substance from *Rhodopseudomonas capsulata*, and by unsaturated fatty acids and related alcohols. FEMS Microbiology Letterd 77, 13–18.

Jacob, F., and Monod, J., 1961, Genetic regulatory mechanisms in the synthesis of proteins, *J. Mol. Biol.*t: 318.

Jassim, S. A. A., Ellison, A., Denyer, S. P., and Stewart, G. S. A. B., 1990, In vivo bioluminescence: a cellular reporter for research and industry, *J. Biolum, Chemilum.* 5: 115.

McKnight, S., and Tjian, R., 1986, Transcriptional selectivity of viral genes in mammalian cells, Cell 46: 795.

Old, R. W., and Primrose, S. B., 1989, Bacteriophage and Cosmid vectors for *E. coli*, in: *Principles of Gene Manipulation* 4th edn., pp. 60–86, Blackwell Scientific Publications.

Park, S. F. and Stewart G. S. A. B. 1990 High efficiency transformation of *Listeria monocytogenes* by electroporation of penicillin treated cells. Gene 94 129–132.

Park, S. F., Nissen U. and Stewart G. S. A. B. 1991 The cloning and expression of luxAB in *Listeria monocytogenes* in: Bioluminescence and Chemiluminescence current status (Stanley, P. E. and Kricka, L. J. eds) pp 35–38 (John Wiley and Sons).

Platt, T., 1986, Transcription termination and the regulation of gene expression, *Annu. Rev, Biochem.* 55: 339.

Ptashne, M., 1986, *A Genetic Switch: Gene Control of Phage Lambda*, Cell Press and Blackwell Scientific Publications, Palo Alto, Calif.

Rabussay, D., and Geiduschek, E. P., 1977, Regulation of gene action in the development of lyric bacteriophages, in: *Comprehensive Virology* 8 (F. C. Wagner, ed.), pp. 1–150, Plenum Press, New York.

Roberts, J. W., 1969, Termination factor for RNA synthesis, *Nature* 224: 1168.

The International Commission on Microbiological Specifications for Foods (ICMSF), *Microorganisms in Foods* 4: Hazard Analysis and Critical Control Point in Microbiological Safety and Quality, ISBN 0 632026510, Blackwell Scientific Publications, Oxford.

Yarmolinsky, M. B., and Sternberg, N., 1988, Bacteriophage P1, in: *The Bacteriophages* 1 (R. Calendar, ed.), pp. 291–438, Plenum Press, New York.

We claim:

1. The method of testing for the presence or concentration of a target bacteria in a fluid sample by the steps of:
   a) adding to the sample bacteriophage capable of infecting the target bacteria under conditions to cause it to infect any target bacteria present.
   b) destroying, removing, neutralizing or inactivating extracellular bacteriophage in the sample,
   c) incubating the sample to complete infection and cause the target bacteria to release the bacteriophage, and
   d) assaying the bacteriophage as an indication of the presence or concentration of the target bacteria in the sample.

2. The method as claimed in claim 1, including between steps c) and d) an additional step
   ci) amplifying, by the use of a permissive bacterial host, the bacteriophage in the sample.

3. The method as claimed in claim 2, wherein the target bacterium is a pathogen.

4. The method as claimed in claim 1 to wherein step b) is performed by subjecting the sample to photon irradiation in the presence of an unsaturated fatty acid.

5. The method as claimed in claim 1 to wherein step b) is performed by means of acetic acid.

6. The method as claimed in claim 5, wherein step a) is performed at a temperature below ambient.

7. The method as claimed in claim 1, wherein the resulting bacteriophage is capable of infecting Listeria monocytogenes and step d) is performed by
   di) using the resulting bacteriophage to infect reporter bacteria which are Listeria monocytogenes genetically engineered to have an indicator gene which is a promotorless lux gene under the expression control of a temporally regulated bacteriophage gene switch which on expression gives rise to luciferase, wherein expression of the indicator gene is initiated by bacteriophage infection of the bacteria and
   dii) observing the detectable polypeptide expressed by the reporter bacteria as an indication of the presence or concentration of the target bacteria in the sample.

* * * * *